United States Patent
Buchold et al.

[11] Patent Number: 5,608,122
[45] Date of Patent: Mar. 4, 1997

[54] PROCESS FOR PREPARING WAX ESTERS AND HYDROGENATION OF WAX ESTERS TO FATTY ALCOHOLS

[75] Inventors: Henning Buchold, Hanau; Fritz-Jürgen Gärtner, Bickenbach; Gert Mallok, Hanau; Eberhard Schlichting, Wehrheim; Hans-Martin Stönner, Eschborn, all of Germany

[73] Assignee: Metallgesellschaft AG, Frankfurt am Main, Germany

[21] Appl. No.: 627,177

[22] Filed: Apr. 3, 1996

[30] Foreign Application Priority Data

Apr. 11, 1995 [DE] Germany ............ 195 13 207.6

[51] Int. Cl.⁶ .................... C07C 29/147; C07C 31/125
[52] U.S. Cl. ........................................................ 568/885
[58] Field of Search ............................................ 568/885

[56] References Cited

FOREIGN PATENT DOCUMENTS

| 749069 | 5/1956 | United Kingdom | 568/885 |
| 9410112 | 5/1994 | WIPO | 568/885 |

Primary Examiner—Joseph E. Evans
Attorney, Agent, or Firm—Herbert Dubno

[57] ABSTRACT

A liquid starting mixture contains at least one fatty acid having 6 to 30 carbon atoms per molecule and per mole of fatty acid comprises 1.0 to 1.5 moles of fatty alcohol having 6 to 30 carbon atoms. An intermediate product which contains at least 50% by weight is prepared from the liquid starting product, which is passed at temperatures from about 120 to 320° C. through a stirring zone and is sprayed and water vapor is removed. The intermediate product is hydrogenated to produce a raw product, which contains at least 75% by weight fatty alcohol. A partial stream which contains fatty alcohol is removed from the raw product and is added to the liquid starting mixture. The intermediate product which contains at least 50% by weight wax ester can be prepared without use of a solids containing catalyst.

12 Claims, 3 Drawing Sheets

PROCESS FOR PREPARING WAX ESTERS AND HYDROGENATION OF WAX ESTERS TO FATTY ALCOHOLS

FIELD OF THE INVENTION

Our present invention relates to a process for producing a fatty alcohol from a liquid starting mixture which contains at least one fatty acid having 6 to 30 carbon atoms per molecule. More particularly, the invention relates to the production of wax esters and the conversion of wax esters to fatty alcohols.

BACKGROUND OF THE INVENTION

German Patent 28 53 990 and the corresponding U.S. Pat. No. 4,259,536 disclose the preparation of fatty alcohols by a catalytic hydrogenation of fatty acids in the liquid phase. From German patent document DE-A-39 13 387 it is known to catalytically hydrogenate liquid fatty acid methyl esters and to prepare a mixture of fatty alcohols and methanol.

OBJECT OF THE INVENTION

It is an object of the invention to prepare fatty alcohols from fatty acids in a process which is particularly inexpensive and permits high yields and in particular can be carried out economically in large plants.

SUMMARY OF THE INVENTION

This object and others which will become apparent hereinafter are attained in accordance with the invention by providing a liquid starting mixture contains per mole of fatty acid 1.0 to 1.5 moles of at least one fatty alcohol containing 6 to 30 carbon atoms per molecule, thereby forming a liquid intermediate product containing at least 50% by weight wax at a temperature in the range from about 120° to 320° C. The liquid starting mixture is passed through at least one stirring zone and a liquid mixture which contains wax ester is sprayed into at least one spraying zone. An atmosphere which contains water vapor is produced in the spraying zone, and is removed at least in part. The intermediate product which contains at least 50% by weight wax ester is hydrogenated to produce a raw product which contains at least 75% by weight fatty alcohol, and a partial stream which contains fatty alcohol is branched from the raw product and is added to the liquid starting mixture.

Because the preparation of an intermediate product consisting of a methyl ester of the fatty acid is intentionally omitted I the process, a hydrogenation of methyl ester is no longer required. It has been found that the esterification of the fatty acids with methanol to form methyl ester is rather expensive because by-products, such as dimethyl ether, must be tolerated and because a catalyst is required.

By contrast, an intermediate product which is rich in wax ester and which is free from any disturbing content of by-products is prepared first in the process in accordance with the invention. The intermediate product which is rich in wax ester may be prepared with or without a catalyst. The preparation without a catalyst is less expensive. An optionally used catalyst may consist, e.g. of a zeolite, as is described in the periodical JAOCS, Volume 69, No. 11 (November 1992) on pages 1150 to 1153.

In the process in accordance with the invention the intermediate product which contains at least 50% by weight and preferably 90% by weight wax ester is hydrogenated to prepare the desired fatty alcohols. That intermediate product can be hydrogenated without difficulty and without or hardly without a formation of by-products (such as methanol).

In theory, the process in accordance with the invention is carried out as follows:

1 mole of fatty acid+1 mole of fatty alcohol are reacted to 1 mole of wax ester+1 mole of water and 2 moles of fatty alcohol are derived as a raw product from 1 mole of wax ester+2 moles of $H_2$. 1 mole of fatty alcohol is branched from the raw product and recycled to the starting mixture.

The intermediate product which is rich in wax ester may be prepared by continuous or batch processing. For the continuous processing it is advantageous to mix in a first reaction zone the fatty acid and the fatty alcohol to form a mixture which contains wax ester and which is passed through at least one further reaction zone, in which the mixture is agitated to effect a stirring. Additionally, the mixture is sprayed in at least one spraying zone.

For the preparation of the wax ester it is important that at least part of the water vapor formed during the esterification is removed from the reaction. This may be effected in various ways. For example the atmosphere which contains water vapor can be sucked off above the mixture. Alternatively, an inert gas, such as nitrogen, may be bubbled through the mixture. The inert gas will effect a stripping and will entrain water molecules from the liquid mixture and from the spraying zone.

It is advantageous to effect a fine atomization of the mixture into the spraying zone to form droplets having preferably a diameter in the range from 0.01 to 5.0 mm.

The ratio of fatty acid to fatty alcohol in the starting mixture may be varied in a wide range. If it is desired to prepare a product which is rich in wax ester and contains only small residual amounts of fatty acid and fatty alcohol, fatty acid and fatty alcohol will be supplied at a mole ratio of 1:1. If it is essential to prepare a wax ester intermediate product which is substantially free from the fatty acid, it is advantageous to start with fatty alcohol in excess so that wax ester having an acid value below 1 or even below 0.1 can be readily prepared. The acid value is measured as usual in mg KOH required to neutralize the residual acid per gram of the sample which is examined.

The intermediate product which contains at least 50% by weight and preferably at least 90% by weight wax ester may be hydrogenated in various ways. In a first method the intermediate product together with hydrogen is caused to flow over a catalyst contained in a fixed bed at temperatures which are usually in the range from 100° to 300° C. and under a pressure from 20 to 4000 bars. This will afford the additional advantage that an adiabatic hydrogenation can be effected so that there will be no need for cooling means in the shaft reactor.

Alternatively, the intermediate product which is rich in wax ester may be hydrogenated in the liquid phase with an addition of hydrogen and an admixing of a fine-grained catalyst. A hydrogenating reactor which can be used for that purpose is described in German Patent 28 53 990.

The method of the invention can comprise the steps of:

(a) reacting a starting mixture of at least one $C_6$ to $C_{30}$ fatty acid with at least one $C_6$ to $C_{30}$ fatty alcohol in a ratio of 1.0 to 1.5 moles of fatty alcohol per mole of fatty acid at a temperature of about 120° to 320° C. at least in part by passing said liquid mixture through at least one stirring zone to produce a wax ester in said liquid mixture;

(b) spraying said liquid mixture produced in step (a) and containing said wax ester into at least one spraying zone to liberate water vapor therefrom and removing at least part of the water vapor liberated from said liquid mixture in said spraying zone, thereby forming an intermediate product containing at least 50% by weight of said wax ester;

(c) hydrogenating said intermediate product to produce a raw product containing at least 75% by weight of fatty alcohol; and (d) branching a partial stream containing fatty alcohol from said raw product and adding said partial stream to the starting mixture.

BRIEF DESCRIPTION OF THE DRAWING

The above and other objects, features, and advantages will become more readily apparent from the following description, reference being made to the accompanying drawing in which.

SPECIFIC DESCRIPTION AND EXAMPLES

The preparation of the intermediate product which is rich in wax ester will be explained first with reference to FIGS. 1 and 2.

Figure 1:
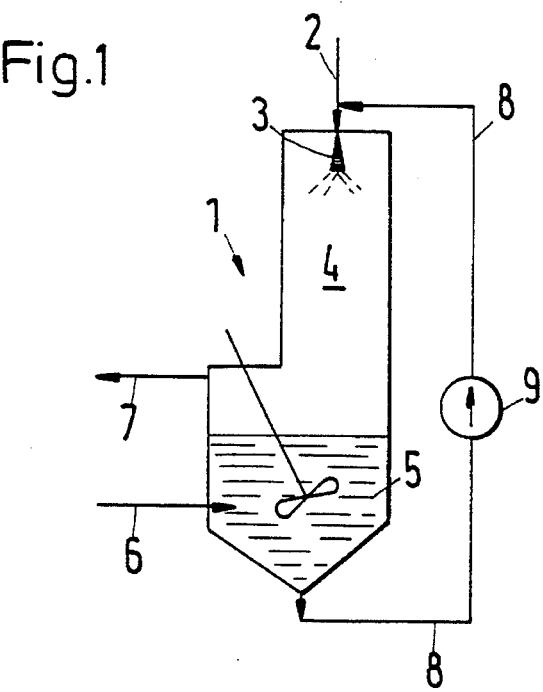
FIG. 1 is a diagrammatic sectional view which illustrates a single-stage process of preparing the intermediate product which is rich in wax ester.

In the process shown in FIG. 1, fatty acid and fatty alcohol are jointly supplied to a reactor 1 through the line 2 and the mixture is sprayed in the form of fine droplets through a nozzle 3 into the spraying zone 4 of the reactor 1. Below the spraying zone 4 the reactor 1 contains a reaction zone 5, in which the mixture consisting of fatty acid, fatty alcohol, and wax ester which has been formed is continuously intensely stirred. An inert gas, such as nitrogen is supplied through line 6 to the mixture. The reaction of fatty acid and fatty alcohol at the temperatures in the range from about 120° to 320° maintained in the reactor involves the formation of water vapor, which is effectively separated from the reaction mixture mainly by the spraying. The water vapor which has been formed and inert gas are jointly withdrawn from the reactor 1 through the line 7, e.g. by being sucked off. Any starting material and wax ester product which are entrained may be recovered by condensation in a known manner, not shown, and may be recycled to the reactor 1.

The liquid which contains wax ester and accumulates in the reaction zone 5 is circulated for some time and by the pump 9 is supplied through line 8 to the top of the reactor 1 and is sprayed again through the nozzle 3. During a batch processing in the reactor 1 the residence times in the reactor are about 1 to 10 hours and the entire amount of liquid is sprayed 1 to 20 times per hour.

Figure 2:
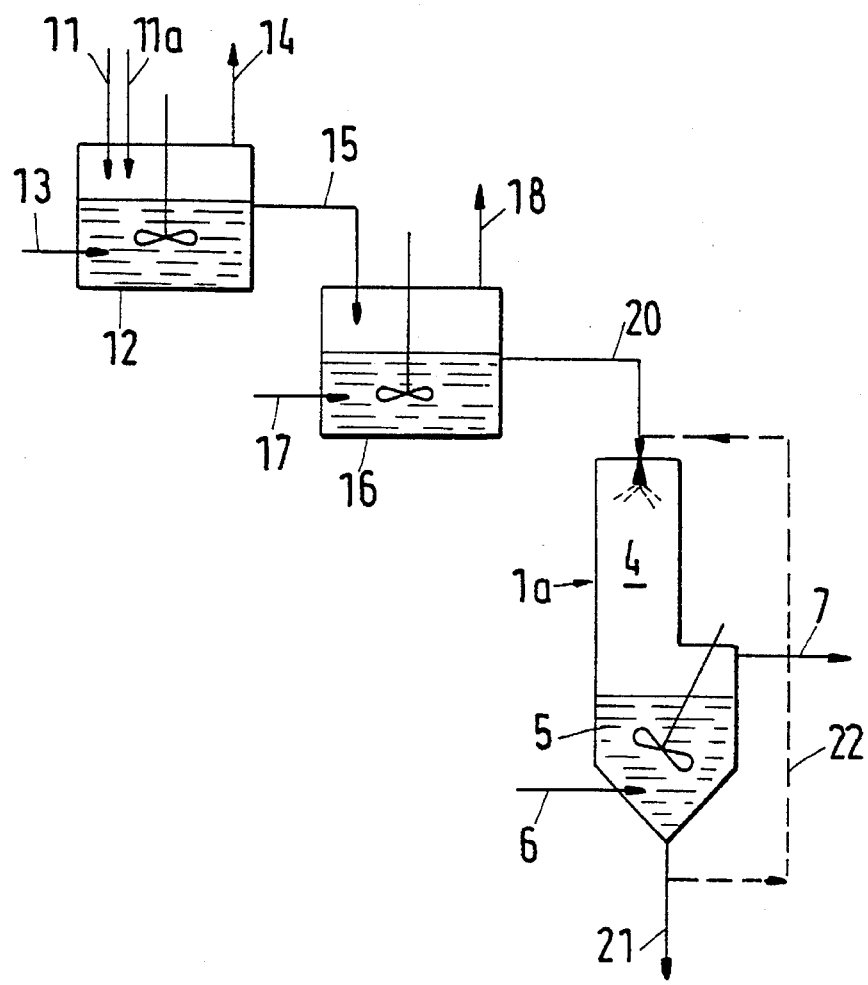
FIG. 2 is a similar view which illustrates a three-stage process of preparing the intermediate product which is rich in wax esters.

The process illustrated in FIG. 2 is particularly suitable for continuous processing. Just as in the process of FIG. 1 a catalyst is usually not required. In accordance with FIG. 2, a first reaction vessel 12 is supplied with fatty acid through line 11 and with a liquid which is rich in fatty alcohol through line 11a and the mixture is intensely stirred in the reaction vessel 12. During the stirring, inert gas, such as nitrogen, is supplied through the line 13. Inert gas containing water vapor is withdrawn through line 14. Only a partial reaction is effected in the first reaction vessel 12 so that a liquid which contains fatty acid, fatty alcohol, and wax ester is withdrawn through line 15 and is processed further in a second reaction vessel 16. In principle, the second vessel can be operated exactly like the first reaction vessel 12 and also comprises an inlet 17 for inert gas and an outlet 18 for a gas which contains water vapor.

The liquid which is withdrawn from the second reaction vessel 16 through line 20 has a higher wax ester content than the liquid in line 15 and contains also residual amounts of fatty acid and fatty alcohol. That liquid is supplied to a reactor 1a. As has been explained with reference to FIG. 1, that reactor 1a contains a spraying zone 4 and a reaction zone 5. Inert gas is supplied through line 6, and a gas which contains water vapor is discharged through line 7. An intermediate product which is rich in wax ester is obtained in line 21. In case of need the reactor 1a may also be operated with a circulation of liquid in that a part of the liquid in line 21 is recycled to the top of the reactor 1a through line 22 indicated by a broken line. Fatty alcohol from line 21 can be fed back to line 11a or to line 15 if desired. In the continuous process illustrated in FIG. 2 the total residence time is usually longer than the residence time in the batch processing illustrated in FIG. 1.

In a modification of FIG. 2 the process may be carried out with only one reaction vessel or with more than two reaction vessels. Also more than one reactor provided with spraying means may be employed.

In the process illustrated in FIG. 3 the intermediate product which is rich in wax ester is prepared in the plant section W, for instance, in the manner which has bee described with reference to FIG. 2. But in a modification the intermediate product may be prepared, e.g. as illustrated in FIG. 1. In the process illustrated in FIG. 3 fatty acid or, more usually, a mixture of fatty acids ($C_6$ to $C_{30}$) is supplied through line 11 to the plant section W and is reacted wit a stream which comes from line 11a and is rich in fatty alcohol. The intermediate product containing at least 50% by weight and preferably at least 90% by weight wax ester is withdrawn in line 21 and together with hydrogen supplied through line 24 is hydrogenated in the shaft reactor 25. The shaft reactor 25 contains a fixed bed 26 consisting of a granular catalyst, which is known per se and has e.g., a copper-base. The particle sizes of the catalyst lie usually in the range from 1 to 30 mm. Temperatures in the range from 100° to 300° C. and a pressure in the range from 20 to 400 bars are maintained in the reactor 25. Hydrogenated raw product together with unreacted hydrogen are withdrawn through line 27 and supplied to a hot-separation vessel 28. Hydrogen is flashed off in the vessel 28 under a slightly lower pressure and is withdrawn in line 29. The hydrogen is recycled to the reactor 25 in line 24 together with fresh hydrogen from line 30.

A raw product containing at least 75% by weight fatty alcohol is withdrawn in line 31 from the separator 28 and is supplied to a flashing vessel 32, from which water vapor formed by side reactions is withdrawn at a low rate through line 33. The remaining raw product is supplied in line 34 to a distillation column 35, from which fatty alcohol is withdrawn as a product in line 36. The bottom product of the distillation column 35 consists of a mixture of fatty alcohols and wax ester and is recycled through line 11a to the plant section W.

Figure 4:
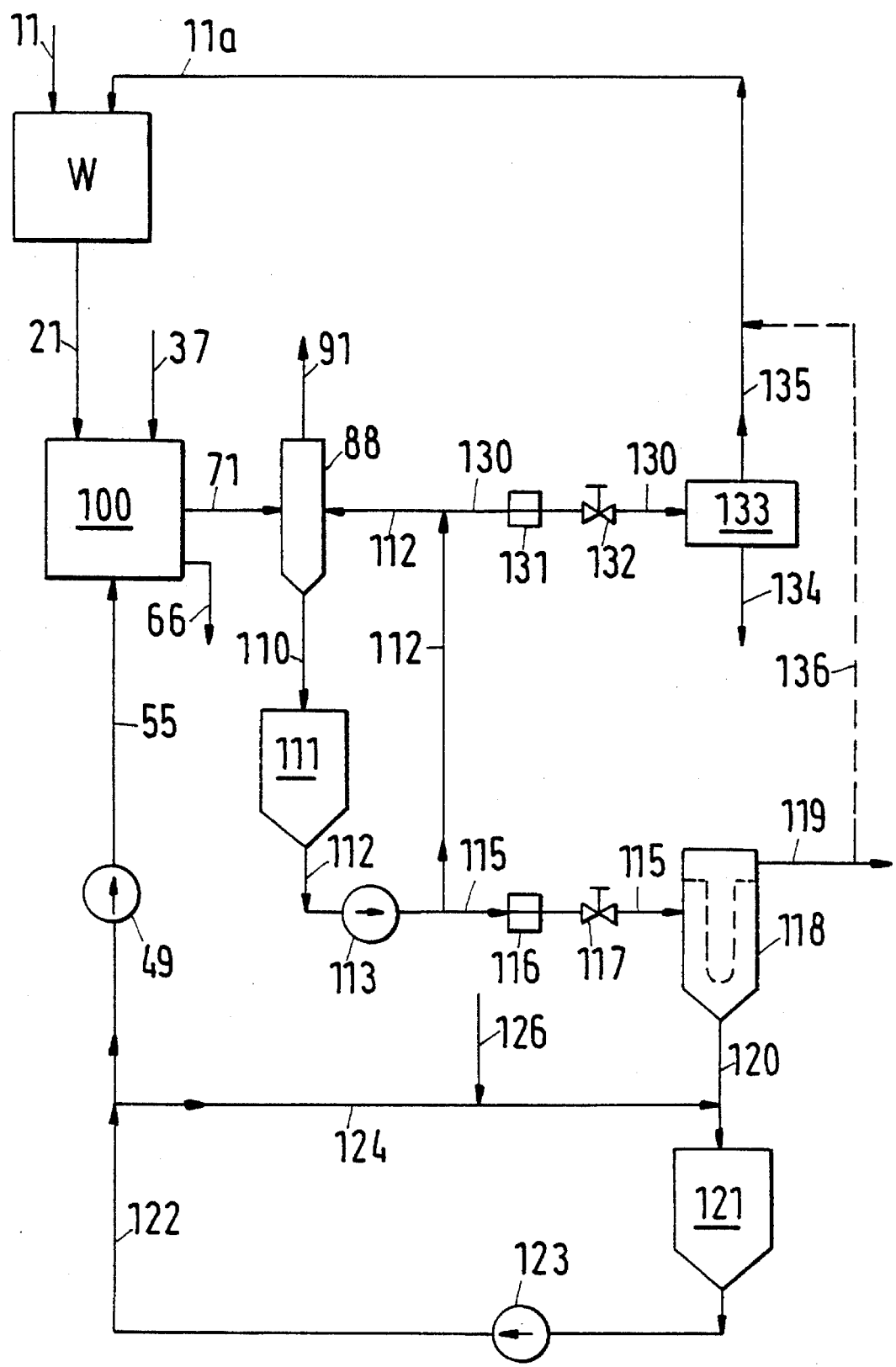
FIG. 4 is a flow-diagram which illustrates a second method of hydrogenating the intermediate product.

In the modified process illustrated in FIG. 4 the intermediate product which is rich in wax ester (line 21) is prepared in the plant section W as described above from fatty acid or a usually employed mixture of fatty acids ($C_6$ to $C_{30}$) and a mixture of fatty alcohol and wax ester which is supplied through line 11a. After an addition of hydrogen from line 37, that intermediate product is catalytically hydrogenated in a liquid phase in the hydrogenation stage 100 at temperatures in the range from 100° to 400° C. and under pressures in the range from 20 to 400 bars. Details of that hydrogenation are described in German Patents 28 53 990 and 43 04 420.

By means of a high-pressure metering pump 49 the hydrogenating stage 100 is supplied through the line 55 with a dispersion which contains fresh and used fine-grained catalyst. A raw product which contains fatty alcohols and used catalyst is withdrawn in line 71 and is first supplied to a flashing vessel 88. Reaction water which is formed at a low rate is withdrawn through line 66. A flashed off gas which contains hydrogen is withdrawn in line 91 and may be recycled entirely or in part to the hydrogenator 100 in a manner which is not shown. The pressure-relieved liquid product obtained in the vessel 88 is conducted inn line 110 to an intermediate vessel 111. A part of the product stream is recycled to the flashing vessel 88 through the recycle line 112 and the circulating pump 113.

A first partial stream of the product stream in the recycle line 112 is branched off through line 115 and conducted through a flow meter 116 and a flow control valve 117 and is then supplied to a filter 118, e.g., a bag filter. In the filter 118, a product is recovered which is rich in fatty alcohol and free of solids and is withdrawn in line 119. That product may be subjected to an ultrafine purification, not illustrated.

A dispersion which contains used catalyst is formed in the filter 118 and is initially supplied through line 120 to an intermediate vessel 121. A part of that dispersion is subsequently supplied by the pre-pressurizing pump 123 through line 122 into the line 55. It is desirable to continuously recycle a part of the dispersion through line 124 to the intermediate vessel 121. Fresh catalyst from lien 126 is admixed at a controlled rate to the dispersion conducted in the line 124 so that a homogeneous distribution of the fresh catalyst in the dispersion is achieved.

A second partial stream of the liquid product is withdrawn from the recycle line 112 through line 130 and through a flow rate meter 131 and a flow control valve 132 is supplied to a decanter 133. The decanter 133 may be replaced by a centrifuge. The decanter 133 discharges in line 134 a phase which is rich in catalyst and which usually contains 50 to 80% by weight solids. That phase may readily be dumped, but may also be processed for re-use. The fatty alcohol formed in the decanter 133 is withdrawn through the line 135 and is recycled through line 11a to the plant section W. If more fatty alcohol is required in W, a part of the product conducted in line 119 is branched off through the line 136 represented by a broken line and is added to the fatty alcohol in line 135. The flow rates of the product streams which are branched off in lines 115 and 130 from the recycle line 112 are variable and usually differing, this flow rate ratio is in the range from 100:1 to 5:1. This flow rate can be changed by an actuation of the flow control valves 117 and 132.

EXAMPLES

In a processing on a laboratory scale, wax ester is first prepared by a batch processing as illustrated in FIG. 1.

A reactor 1 having an electrically heatable jacket is supplied with 208 g of a mixture of fatty acids ($C_8$ to $C_{18}$) having an average molecular weight of 208 together with 1.1 moles $C_{16}$-fatty alcohol. The reactants are supplied at a temperature of 65° C. The mixture has an acid value of 117 mg KOH/g. The temperature in the reactor is 250° C. Nitrogen as an inert gas is supplied through line 6. Liquid at a rate of 6 liters per hour is sprayed into the spraying zone 4 through nozzle 3 as droplets having a size in the range from 0.01 to 1.0 mm. After 3 hours a virtually complete esterification has been effected and the wax ester product has an acid value of 0.09, a saponification number of 135 mg KOH/g, and the molecular weight 422. That wax ester is used in the examples which will be described hereinafter.

Example 1

Figure 3:
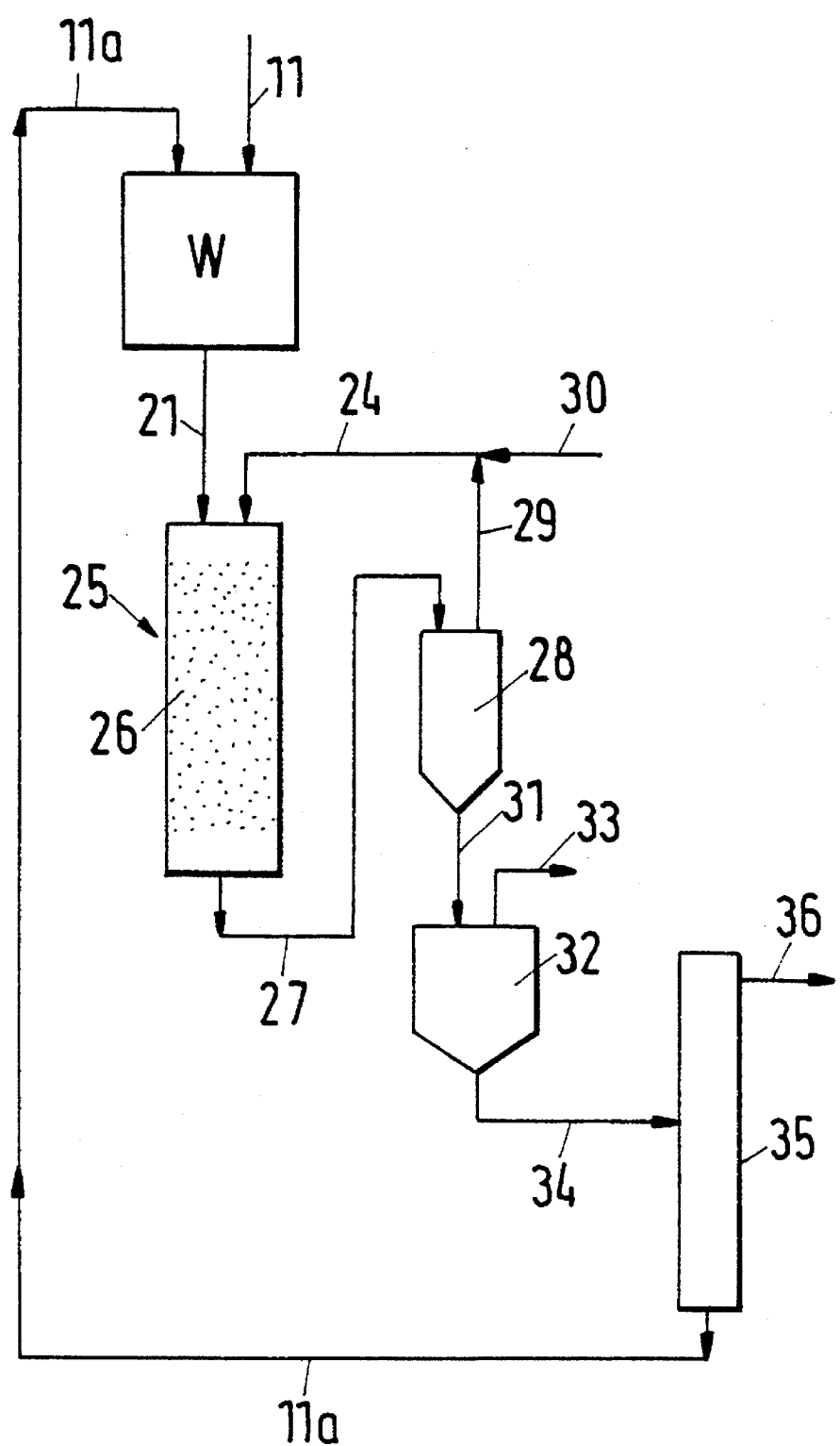
FIG. 3 is a flow diagram of a first method of hydrogenating the intermediate product.

The hydrogenation is effected in the laboratory in a manner which is similar to that illustrated in FIG. 3. In a tubular reactor, 400 ml hydrogenating catalyst constitute a fixed bed, which is 30 mm in diameter and has a height of 200 mm. The catalyst is of the Type T 4489 A (made by Süd-Chemie, Munich, Germany) and consists of tablets of 3 mm×3 mm. The reactor has an electrically heated jacket and is operated at 230° C. and a pressure of 300 bars and with a wax ester throughput rate of 750 ml/h and a supply of $H_2$ at a rate of 3.185 sm$^3$/h (sm$^3$=standard cubic meter).

The hydrogenated end product is formed without recycling and consists of 96.6% fatty alcohol and 3.4% by weight wax ester. A rectification produces a head product consisting of pure fatty alcohol and in a bottom product consisting of fatty alcohol and wax ester. That bottom product may be used to prepare wax ester in a plant W and has a saponification number of 4.6 and a hydrocarbon content of 0.75% by weight.

Example 2

The wax ester which has already been used in Example 1 is then hydrogenated by a batch processing in a liquid phase containing a stirred-in catalyst. The reaction vessel consists of a 2-liter stirred autoclave. 20 g of a catalyst powder of the Type G 99 B-13 (Süd-Chemie) are used per 400 g of wax ester. $H_2$ is supplied through a high-pressure compressor. A temperature of 298° C. and a pressure of 300 bars are maintained in the autoclave and stirring is effected at 1000 revolutions per minute. In the following table the results of the hydrogenation are stated in dependence on the reaction time T, also the saponification number SN of the liquid in the autoclave is given in mgKOH/g and the conversion C of the wax ester is given in % by weight.

| T(min) | 0 | 2 | 4 | 8 | 10 | 13 | 15 | 60 |
|---|---|---|---|---|---|---|---|---|
| SN | 135 | 45.4 | 19.8 | 7.15 | 6.7 | 3.9 | 3.3 | 1.4 |
| C | 0 | 66.6 | 85.4 | 94.7 | 95.1 | 97.1 | 97.6 | 99 |

The end product has a saponification number of 0.08 and a hydrocarbon content of 0.5% by weight.

We claim:

1. A process for producing a fatty alcohol comprising the steps of:

(a) reacting a starting mixture of at least one $C_6$ to $C_{30}$ fatty acid with at least one $C_6$ to $C_{30}$ fatty alcohol in a ratio of 1.0 to 1.5 moles of fatty alcohol per mole of fatty acid at a temperature of about 120° to 320° C. at least in part by passing said liquid mixture through at least one stirring zone to produce a wax ester in said liquid mixture;

(b) spraying said liquid mixture produced in step (a) and containing said wax ester into at least one spraying zone to liberate water vapor therefrom and removing at least part of the water vapor liberated from said liquid mixture in said spraying zone, thereby forming an intermediate product containing at least 50% by weight of said wax ester;

(c) hydrogenating said intermediate product to produce a raw product containing at least 75% by weight of fatty alcohol; and (d) branching a partial stream containing fatty alcohol from said raw product and adding said partial stream to the starting mixture.

2. The process defined in claim 1 wherein said intermediate product is formed without use of a solids-containing catalyst.

3. The process defined in claim 2, further comprising the step of introducing an inert gas to said stirring zone to purge water vapor from said liquid mixture therein.

4. The process defined in claim 3, further comprising the step of maintaining an excess of fatty alcohol in said mixture to obtain said intermediate product virtually free from acid.

5. The process defined in claim 4 wherein said intermediate product is hydrogenated in liquid-phase hydrogenation in the presence of a fine-grained solid hydrogenation catalyst admixed with the intermediate product.

6. The process defined in claim 4 wherein the intermediate product is hydrogenated by passing the intermediate product and hydrogen over a fixed-bed catalyst.

7. The process defined in claim 6 wherein the hydrogenation is carried out adiabatically on the fixed bed.

8. The process defined in claim 1, further comprising the step of introducing an inert gas to said stirring zone to purge water vapor from said liquid mixture therein.

9. The process defined in claim 1, further comprising the step of maintaining an excess of fatty alcohol in said mixture to obtain said intermediate product virtually free from acid.

10. The process defined in claim 1 wherein said intermediate product is hydrogenated in liquid-phase hydrogenation in the presence of a fine-grained solid hydrogenation catalyst admixed with the intermediate product.

11. The process defined in claim 1 wherein the intermediate product is hydrogenated by passing the intermediate product and hydrogen over a fixed-bed catalyst.

12. The process defined in claim 11 wherein the hydrogenation is carried out adiabatically on the fixed bed.

* * * * *